US012016792B2

(12) United States Patent
Chodorow (10) Patent No.: US 12,016,792 B2
(45) Date of Patent: Jun. 25, 2024

(54) BRUXISM TREATMENT APPARATUS

(71) Applicant: Sacks Holdings, Inc., San Diego, CA (US)

(72) Inventor: Devin S. Chodorow, San Diego, CA (US)

(73) Assignee: Sacks Holdings, Inc., San Diego, CA (US)

( * ) Notice: Subject to any disclaimer, the term of this patent is extended or adjusted under 35 U.S.C. 154(b) by 328 days.

(21) Appl. No.: 16/170,932

(22) Filed: Oct. 25, 2018

(65) Prior Publication Data
US 2019/0117442 A1  Apr. 25, 2019

Related U.S. Application Data

(60) Provisional application No. 62/577,122, filed on Oct. 25, 2017.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ........ A61F 2005/563; A61F 5/58; A61F 5/56; A61F 5/566; A61C 5/90; A61C 7/00; A61C 7/08; A61C 7/10; A61C 7/36; A61C 5/80; A61C 5/82; A63B 71/085; A63B 2071/086; A63B 2071/088; A63B 71/08; Y10S 602/902; A61B 5/4557; A61B 5/45; A61B 5/4538; A61B 5/4542
USPC .............. 128/859–862, 848; 433/6–7, 36–37
See application file for complete search history.

(56) References Cited

U.S. PATENT DOCUMENTS

| 4,976,618 A | 12/1990 | Anderson |
| 5,031,611 A | 7/1991 | Moles et al. |
| D373,421 S | 9/1996 | Brown |
| 5,584,687 A | 12/1996 | Sullivan et al. |
| D397,442 S | 8/1998 | Kittelsen |
| 5,873,365 A | 2/1999 | Brown |
| D406,405 S | 3/1999 | Yoshida |
| 6,152,138 A | 11/2000 | Brown et al. |
| 6,536,424 B2 | 3/2003 | Fitton et al. |

(Continued)

FOREIGN PATENT DOCUMENTS

WO    2012/153066    11/2012

OTHER PUBLICATIONS

Final Office Action for U.S. Appl. No. 14/546,944 dated Apr. 5, 2017, 22 pages.

(Continued)

*Primary Examiner* — Rachael E Bredefeld
*Assistant Examiner* — Trisha Talapatra
(74) *Attorney, Agent, or Firm* — Kilpatrick Townsend & Stockton LLP (57) ABSTRACT

An intraoral device is disclosed. The device includes a curved portion configured to extend along a user's teeth, and first and second back portions connected to the curved portion. In addition, the device includes a first projection extending from a first back portion and the second projection extending from the second back portion. In some embodiments, the projections are positioned such that, when in the user's mouth, the projections are between upper and lower teeth of the user.

19 Claims, 8 Drawing Sheets

(56) References Cited

U.S. PATENT DOCUMENTS

| | | | |
|---|---|---|---|
| 6,626,180 B1* | 9/2003 | Kittelsen | A63B 71/085 128/862 |
| 6,978,786 B2 | 12/2005 | Sabbagh | |
| 7,490,609 B2 | 2/2009 | Brown | |
| 7,506,651 B2* | 3/2009 | Anonsen | B63C 11/186 128/846 |
| 7,832,404 B2* | 11/2010 | Jansheski | A61F 5/566 128/859 |
| 8,196,587 B2 | 6/2012 | Chodorow | |
| 8,201,560 B2 | 6/2012 | Dembro | |
| 8,578,940 B1* | 11/2013 | Van Essen | A61C 5/90 128/859 |
| 8,701,673 B2 | 4/2014 | Chodorow | |
| 8,733,364 B2 | 5/2014 | Chodorow | |
| 10,342,694 B1* | 7/2019 | Mowell | A61F 5/566 |
| D869,658 S | 12/2019 | Chodorow | |
| 2004/0107970 A1* | 6/2004 | Kittelsen | A63B 71/085 128/859 |
| 2009/0165805 A1* | 7/2009 | Syrop | A63B 71/085 128/861 |
| 2010/0206314 A1 | 8/2010 | Brown et al. | |
| 2011/0004129 A1 | 1/2011 | Wavle et al. | |
| 2011/0139162 A1 | 6/2011 | Chodorow | |
| 2012/0283069 A1 | 11/2012 | Martin et al. | |
| 2012/0285473 A1* | 11/2012 | Wright | A63B 71/085 128/862 |
| 2014/0238419 A1 | 8/2014 | Lovat et al. | |
| 2015/0133269 A1 | 5/2015 | Landis et al. | |
| 2015/0209645 A1* | 7/2015 | Zents | A63B 71/085 128/861 |
| 2015/0305918 A1 | 10/2015 | Chodorow et al. | |
| 2016/0001160 A1 | 1/2016 | Engel | |
| 2019/0117442 A1 | 4/2019 | Chodorow | |

OTHER PUBLICATIONS

Non Final Office Action for U.S. Appl. No. 14/546,944 dated May 22, 2018, 13 pages.

Non-Final Office Action for U.S. Appl. No. 14/546,944 dated Oct. 19, 2016, 18 pages.

Non-Final Office Action for U.S. Appl. No. 29/623,580 dated Oct. 30, 2018, 11 pages.

Final Office Action for U.S. Appl. No. 14/546,944 dated Dec. 27, 2018, 16 pages.

Notice of Allowance for U.S. Appl. No. 14/546,944 dated Dec. 18, 2019, 13 pages.

Notice of Allowance for U.S. Appl. No. 29/623,580 dated Jul. 31, 2019, 6 pages.

* cited by examiner

BRUXISM TREATMENT APPARATUS

CROSS-REFERENCES TO RELATED APPLICATIONS

This application claims the benefit of U.S. Provisional Application No. 62/577,122, filed Oct. 25, 2017, and entitled, "Bruxism Treatment Apparatus", the entirety of which is hereby incorporated by reference herein.

FIELD OF THE INVENTION

The present invention relates, generally, to dental protection devices, and, more particularly, to bruxism protection and treatment devices.

BACKGROUND OF THE INVENTION

Bruxism is a term that refers to excessive grinding and clenching of the teeth. Those with bruxism are often unaware that they have developed this habit, and often do not know that treatment is available until damage to the mouth and teeth has been done. Each individual may experience different symptoms which may include: abraded teeth, facial pain, oversensitive teeth, tense facial and jaw muscles, headaches, dislocation of the jaw, damage to the tooth enamel, exposing the inside of the tooth (dentin), a popping or clicking in the temporomandibular joint (TMJ), tongue indentations, and/or damage to the inside of the cheek.

While the causes of bruxism are sometimes not known or not recognized, oral health specialists often point to excessive stress and certain personality types as being associated with bruxism. Bruxism often affects persons with nervous tension such as anger, pain, or frustration, and/or persons with aggressive, hurried, or overly competitive tendencies.

Bruxism may be diagnosed during dental examinations, and may, for example, be indicated by the upper surfaces of the teeth appearing flat. If symptoms are present, the condition is usually observed for changes over the next several visits before a treatment program is established.

Specific treatment for bruxism may be determined by a dentist or physician based on one or more factors, such as the person's age, overall health, medical history, severity of symptoms, patient or doctor preference, and tolerance for specific medications, procedures, or therapies.

In many cases bruxism can be successfully treated by:
a. Behavior modification achieved through instruction from an expert regarding helping the patient learn to rest his/her tongue, teeth, and lips properly, and/or how to rest his/her tongue upward while keeping the teeth apart and lips closed to relieve discomfort on the jaw.
b. A specially-fitted plastic mouth appliance may be worn at night to absorb the force of biting. This appliance may help to prevent future damage to the teeth and aid in changing the patient's behavior.
c. Biofeedback which involves an electronic instrument that measures the amount of muscle activity of the mouth and jaw—indicating to the patient when too much muscle activity is taking place so that the behavior can be changed. This is especially helpful for daytime bruxers.

Bruxism patients may present with a variety of symptoms, including anxiety, stress, tension, depression, earache, eating disorders, insomnia, headache and/or jaw pain. Eventually, bruxing shortens and blunts the teeth being ground, and may lead to myofacial muscle pain, temporomandibular joint dysfunction and headaches. In severe, chronic cases, it can lead to arthritis of the temporomandibular joints. The jaw clenching that often accompanies bruxism can be an unconscious neuromuscular daytime activity, which should be treated as well, usually through physical therapy, such as recognition and stress response reduction.

Prior art bruxism management techniques include minimizing the abrasion of tooth surfaces by the wearing of an acrylic dental guard or splint, designed to the shape of an individual's upper or lower teeth from a bite mold. Mouth guards are obtained through visits to a dentist for measuring, fitting, and ongoing supervision. These devices use one or more of four approaches: constraint of dental movement such that serious damage to the temperomandibular joints is prevented, stabilization of occlusion by minimizing the gradual changes to the positions of the teeth that typically occur with bruxism, prevention of tooth damage, and the enabling of a bruxism practitioner to judge in broad terms the extent and patterns of bruxism, for example, through examination of physical indentations on the surface of a worn dental guard. Dental guards typically worn over an extended period during many night's sleep, may be seen in U.S. Pat. Nos. 4,976,618, 5,873,365, and 6,152,138. Another type of device sometimes given to a bruxer is a repositioning splint which may look similar to a traditional night guard, but is designed to change the occlusion or "bite" of the patient.

Bruxism is associated with a person's mandible which is connected to the cranium by the temporomandibular joints located immediately in front of the ears. Rotation of the mandible about these joints is accomplished by the masticatory muscles, each of which extends from an opposite side of the mandible to a connecting point on the cranial bones. The masticatory muscles have an at rest position between their extended and contracted states. Under normal physiological conditions involving the outgrowth of a full complement of teeth, the mandibular portion of each temporomandibular joint will rest lightly in the cranial portion of the joint, and the muscles will be relaxed or at rest.

Masticatory muscle related strain and/or pain can arise due to differences in occlusal pressures along the upper and lower dental arches. Temporomandibular joint dysfunction syndrome relates to occlusion-muscle incompatibility. Masticatory muscle accommodation is a key factor in the etiology of this syndrome. Psychological tension and stress can lead to temporomandibular joint dysfunction or bruxism in otherwise stable mouths with normal occlusion.

The most frequent jaw movement involves elevation of the mandible from its rest position into centric occlusion. Simple elevation of the mandible is normally powered almost entirely by the elevator muscles, other muscles providing only a minor bracing action. The bilateral temporals, masseters and medial pterygoids provide an excess supply of elevator motor units. Since these motor units alternate in function, with fatigued units relaxing to rest while others take their place, mandible elevation can be continued over long periods of time without over fatiguing these muscles.

Occlusion-muscle dysfunction alters this condition drastically because accommodation has a highly selective effect on the masticatory muscles, increasing their activity disproportionately in certain areas of the bilateral complex. In the presence of occlusion muscle disharmony, a traumatic closure into centric occlusion requires that the mandible be adjusted every time it is elevated into occlusion. If, for example, the required adjustment is horizontal, the muscle areas capable of producing such horizontal movements must be called into activity with the same frequency as are the elevator muscle areas. Unfortunately, there are far fewer of these horizontal-adjustor motor units than elevator motor units.

Ultimately the functional capacity of these comparatively few horizontal motor units is exceeded, which triggers an exhaustion-in coordination-spasm sequence and development of the temporomandibular joint syndrome symptoms. The resulting tenderness and spasms are found most frequently in the lateral pterygoid muscles which function as anterior adjustors of mandibular placement.

In psychological stress related syndromes the muscles become fatigued as a result of nocturnal clenching or grinding of the teeth. These nocturnal activities give rise to the same symptoms as malocclusion-based temporomandibular joint dysfunction.

The sequence of muscle dysfunction can spread beyond the masticatory muscles, producing a constellation of primary symptoms of the temporomandibular joint pain-dysfunction syndrome. These symptoms include pain and/or tenderness in the temporomandibular joint area or masticatory muscles; "clicking" in the temporomandibular joint; limitation of jaw opening; restriction of jaw movement; and secondary symptoms which are medical in nature, being transmitted to other, more distant areas of the head and neck. These secondary symptoms probably include some of the most widespread and problematic conditions medicine has to deal with, namely, headache (including "tension" headaches), atypical facial neuralgias, tinnitus and neck and ear pain, among others. Also, certain neuromuscular disorders of the face, head and neck, shoulders, back, arms and hands can occur. These secondary symptoms are functional disturbances which exhibit no organic changes in the affected tissues, making diagnosis difficult. They are often ill-defined and difficult for the patient to describe.

These symptoms are usually diagnosed as purely medical in nature because they occur at some distance from the teeth. Their masticatory muscle origin unfortunately is not readily apparent. The usual result is that treatment is mistakenly directed to the secondary symptom's locale rather than to the underlying malocclusion. Such malocclusions are common but difficult to detect. Intercuspation of the teeth appears normal, while the underlying faulty (accommodation-necessitating) craniomandibular relationship is hidden by the automatic compensatory action of the muscles. The secondary symptoms resulting from temporomandibular joint dysfunction thus are usually treated palliatively instead of having their basic cause eliminated. For malocclusion-based muscle dysfunction, definitive therapy is essentially an orthopedic procedure and requires correction of the faulty cranio-mandibular relationship by a dentist. For psychological stress-related dysfunctions, treatment may be addressed in other ways.

Some notable prior art methods of treating temporomandibular joint dysfunction and bruxism include clinical monitoring devices to measure the amount of pressure being asserted, splints to be worn during sleep to prevent the wearing of teeth, and behavior modification devices, which provide an electrical shock to the jaw muscles to interrupt nocturnal bruxing episodes without waking the patient.

SUMMARY OF THE INVENTION

One aspect of the present disclosure relates to a dental apparatus. The dental apparatus includes: a curved portion; first and second back portions connected to the curved portion; and a first projection extending inwardly from the first back portion and second projection extending inwardly from the second back portion. In some embodiments, each of the first and second projections includes a top portions separated from a bottom portion by a connecting member. In some embodiments, the top portion of the first projection connects to the first back portion. In some embodiments, the bottom portion of the first projection is unconnected to the first back portion.

In some embodiments, the top portions and the bottom portions are non-parallel. In some embodiments, the connecting members extend from a back towards a front of each of the first and second projections. In some embodiments, the connecting members partially extend from a back towards a front of each of the first and second projections. In some embodiments, the partial extension of the connecting members from the back towards the front of the first and second projections creates a first portion and a second portion of each of the first and second projections. In some embodiments, the top portion is rigidly connected to the bottom portion of each of the first and second projections in the first portion. In some embodiments, the top portion and the bottom portion are non-rigidly connected in the second portion.

In some embodiments, the connecting members fully extend from a back towards a front of each of the first and second projections. In some embodiments, the connecting member can be a wedge shaped member. In some embodiments, the space between the top portion and the bottom portion of the first and second projections is non-constant between the back and the front of each of the first and second projections. In some embodiments, the space between the top portion and the bottom portion of the first and second projections progressively increases from the back to the front of each of the first and second projections. In some embodiments, the distance between the top portion and the bottom portion of the first and second projections is greater at the front of each of the first and second projections than at the back of each of the first and second projections. In some embodiments, the dental apparatus further includes a lip partially extending around the bottom portion. In some embodiments, the bottom portion of first projection is only coupled to the first back portion via the connection member.

One aspect of the present disclosure relates to a bruxism device. The bruxism treatment device includes: a first back portion; a second back portions; and a pair of projections. The pair of projections include: a first projection extending inwardly from the first back portion; and a second projection extending inwardly from the second back portion. In some embodiments, each of the first and second projections include a top member separated from a bottom member by a wedge-shaped connecting member connecting the top member to the bottom member. In some embodiments, the bottom member of the first projection is unconnected to the first back portion.

In some embodiments, the bottom member of first projection is only coupled to the first back portion via the connection member. In some embodiments, the top members and the bottom members are non-parallel. In some embodiments, the connecting members extend from a back towards a front of each of the first and second projections. In some embodiments, the connecting members partially extend from a back towards a front of each of the first and second projections. In some embodiments, the partial extension of the connecting members from the back towards the front of the first and second projections creates a first portion and a second portion of each of the first and second projections. In some embodiments, the top member is rigidly connected to the bottom member of each of the first and second projections in the first portion.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION OF THE INVENTION

Embodiments of the present invention include an intraoral device to be used, for example, when a person sleeps. The device is positioned between the person's upper and lower teeth to reduce symptoms and damage caused, for example, by bruxism and temporomandibular dysfunction. It is effective, very simple to use and relatively low in cost.

For the purposes of explanation, the ensuing details are set forth in order to provide a thorough understanding of various embodiments. It will be apparent, however, to one skilled in the art that various embodiments may be practiced without some of these specific details. For example, various features may be shown as components of some specific embodiments. In other instances, previously known features may be shown without unnecessary detail in order to avoid obscuring the inventive features of the described embodiments.

Embodiments provided herein are examples only, and are will not intended to limit the scope, applicability, or configuration of the disclosure. Rather, the ensuing description of the embodiments will provide those skilled in the art with an enabling description for implementing one or more embodiments. It should be understood that various changes may be made in the function and arrangement of elements without departing from the spirit and scope of the disclosed embodiments.

Figure 1:
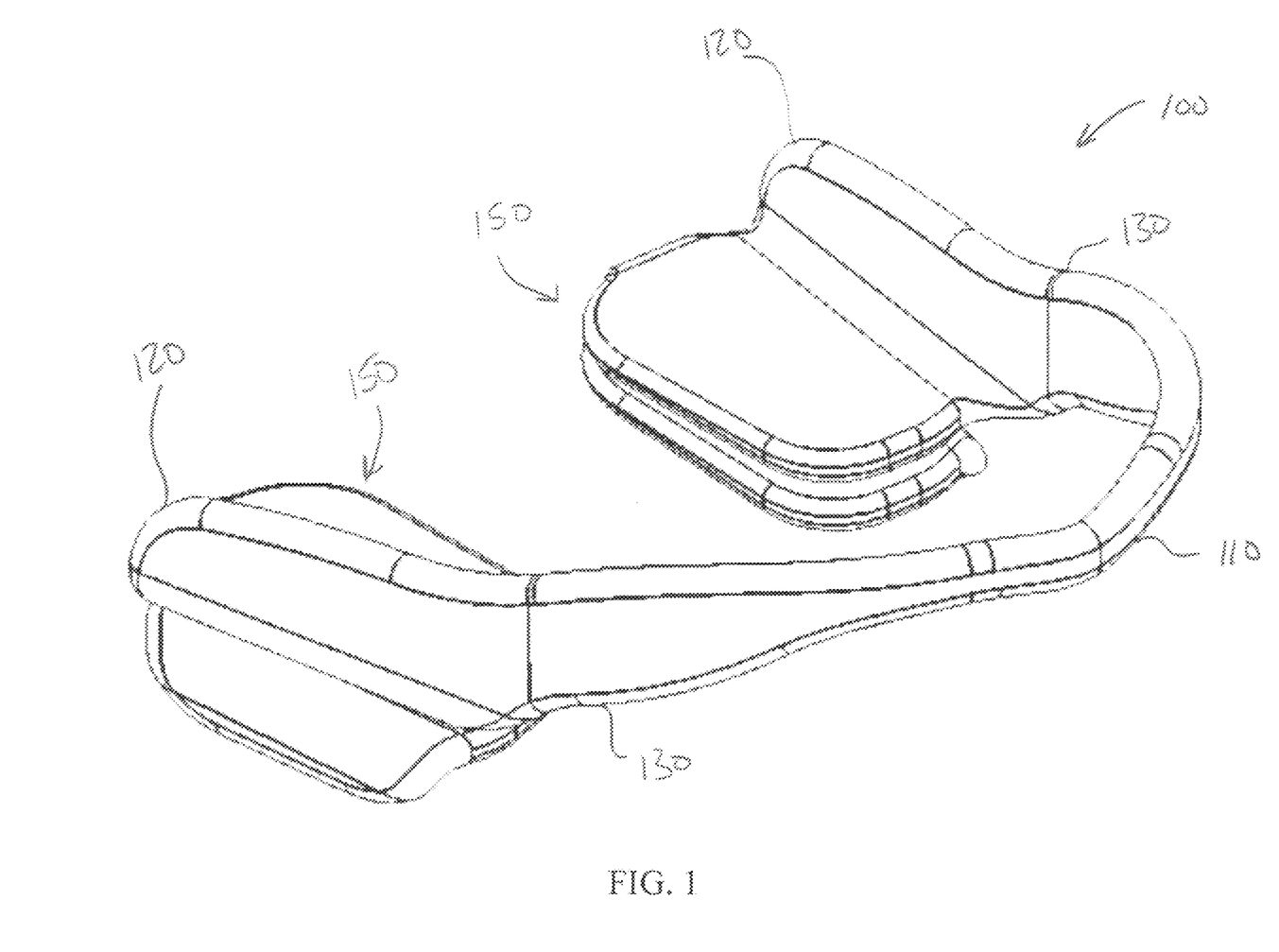
FIG. 1 is a perspective view of one embodiment of a bruxism treatment apparatus.

FIG. 1 is a perspective view of one embodiment of a dental apparatus 100 according to some embodiments. In some embodiments, the dental apparatus 100 can be a bruxism treatment apparatus. As shown, dental apparatus 100 comprises a curved portion 110, and first and second back portions 120. In some embodiments, the dental apparatus 100 is symmetric across a plane extending through the mid-point of the curved portion 110 and between the first and second back portions 120. In addition, first and second back portions 120 are connected to curved portion 110 by connection arms 130. In some embodiments, each of the first and second back portions 120 are connected to a unique one of the ends of the curved portion 110, and in some embodiments, each of the first and second back portions 120 are connected to a unique one of the ends of the curved portion 110 via a unique connection arm 130. In some embodiments, this connection between the first and second back portions 120 and unique ends of the curved portion 110 can give the dental apparatus 100 a U-shape, with the curved portion 110 forming the base of the U and the first and second back portions 120 forming the straight portions of the U.

The back portions 120 can comprise a variety of shapes and sizes. In some embodiments, the back portions 120 can comprise substantially planar members that are sized to fit comfortably between the teeth and the gums, and in some embodiments, between the teeth, gums, and cheeks of the user.

In some embodiments, the curved portion 110 and the connection arms 130 are sized and shaped such that the back portions 120 are offset from the curved portion 110. As further seen in FIG. 1, projections 150 respectively extend from either of the first and second back portions 120.

The dental apparatus 100 can comprise a variety of shapes and sizes and can be made from a variety of materials. In some embodiments, dental apparatus 100 is a one-piece molded device formed with a flexible and resilient plastic such as a thermoplastic elastomer, for example DuPont's Elvaloy™, PVC, silicones, and other plastics and polymers. Desired softness-toughness and resilient cushion characteristics may be achieved, for example, with material of Durometer index 00-A on the Shore scale. In some embodiments, the dental apparatus 100 is formed with a laminate having a soft surface and a tougher inner layer.

The curved portion 110 can comprise a variety of shapes and sizes. In some embodiments, the curved portion 110 is curved to generally match the curvature of a person's teeth and is sized to comfortably fit between the front teeth and gums of the person. In some embodiments, the curved portion 110, the connection arms 130, and the first and second back portions 120 are sufficiently pliable to effectively conform and fit to jaws of different sizes and curvatures.

In some embodiments, a user places the dental apparatus 100 into their mouth, such that the curved portion 110, the connection arms 130, and the first and second back portions 120 extend along and around surfaces of the gums and teeth facing out of the mouth. In addition, in this embodiment, when in place, the projections 150 extend from the first and second back portions 120 toward the interior of the mouth, such that the projections 150 are between upper and lower teeth.

In alternative embodiments, a user may place a dental device into their mouth, such that a curved portion, connection arms, and first and second back portions of the dental device extend along surfaces of the gums and teeth facing the interior of the mouth. In addition, in this embodiment, projections of the dental device extend from first and second back portions toward the exterior of the mouth, such that the projections are between upper and lower teeth.

In some embodiments, the user places the dental apparatus 100 into their mouth such that the curved portion 110, the connection arms 130, and the first and second back portions 120 extend along and around surfaces of the upper gums and teeth. Alternatively, in some embodiments, the user places the dental apparatus 100 into their mouth such that the curved portion 110, the connection arms 130, and the first and second back portions 120 extend along and around surfaces of the lower gums and teeth.

The projections 150 can comprise a variety of shapes and sizes. In some embodiments, there can be any desired number of projections of each of the first and second back portions 120. In one embodiment, for example 1, 2, 3, 4, 5, 6, 7, 8, 9, 10, 15, 20, or any other or intermediate number of projections 150 can extend from the first and second back portions 120. In some embodiments, the projections 150 are compressible and cushion compressive forces between upper and lower teeth with a resistive force and return to their uncompressed state once the compressive forces are removed. Compression, deflection, and/or deformation of the projections 150 may occur in response to the compressive forces. The compression, deflection, and/or deformation of the projections 150 occurs because of, for example, the properties of the materials from which the projections 150 are made and because of the geometry of the projections. In some embodiments, plastic deformation occurs, such that the projections 150 are reshaped so as to conform to the topology of the user's teeth. In alternative embodiments, plastic deformation does not occur, such that the projections 150 only temporarily deform and return to their original shape when the compressive forces are removed.

Figure 2:
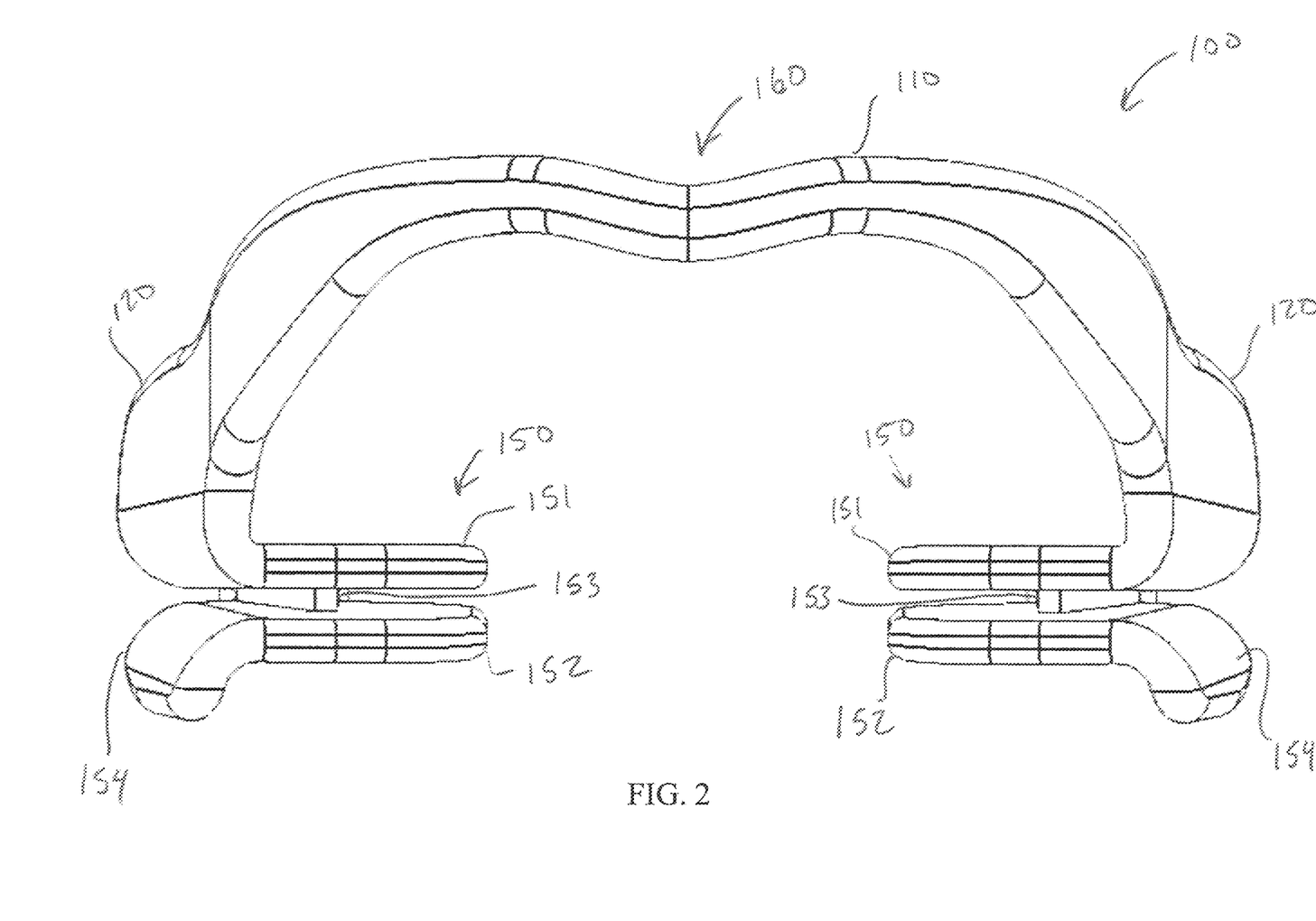
FIG. 2 is a front view of one embodiment of the bruxism treatment apparatus.

FIG. 2 is a front view of the dental apparatus 100. As seen, the first and second back portions 120 are connected to the curved portion 110 by the connection arms 130. Furthermore, the projections 150 respectively extend from either of the first and second back portions 120. As further shown in FIG. 2, at the center of the curved portion 110 is a recess 160 formed by a bend in the curved portion 110. The recess 160 is configured to substantially align with, but not contact or rub against the user's upper or lower lip frenulum, depending on the orientation of the dental apparatus 100 in the wearer's mouth.

The projections 150 each comprise a top portion 151, also referred to herein as a top plate 151, extending inward and towards the projection 150 on the other of the back portions 120 of the dental apparatus 110 and a bottom portion 152, also referred to herein as a bottom plate 152, likewise extending inwards and towards the projection 150 of the other of the back portions 120 of the dental apparatus 110. The dental apparatus 100 can be worn so that the top portion 151 of the projections 150 contact the upper teeth in the wearer's mouth, or the dental apparatus 100 can be worn so that the top portion 151 of the projections 150 contact the lower teeth in the wearer's mouth. The top portion 151 directly connects to the back portion 120 and connects to the bottom portion 152 via a connecting member 153. The bottom portion 152 does not directly connect to the back portion, nor does the bottom portion 152 extend from the back portion 120, rather, the bottom portion 152 connects to the connecting member 153 and/or the top portion 152. The bottom portion 152 further comprises a lip 154. In some embodiments, the lip 154 can facilitate in preventing movement of the dental apparatus 100 while being worn, and specifically, can minimize risk of twisting. In some embodiments, the lip 154 partially extend around the bottom portion 152.

Figure 3:
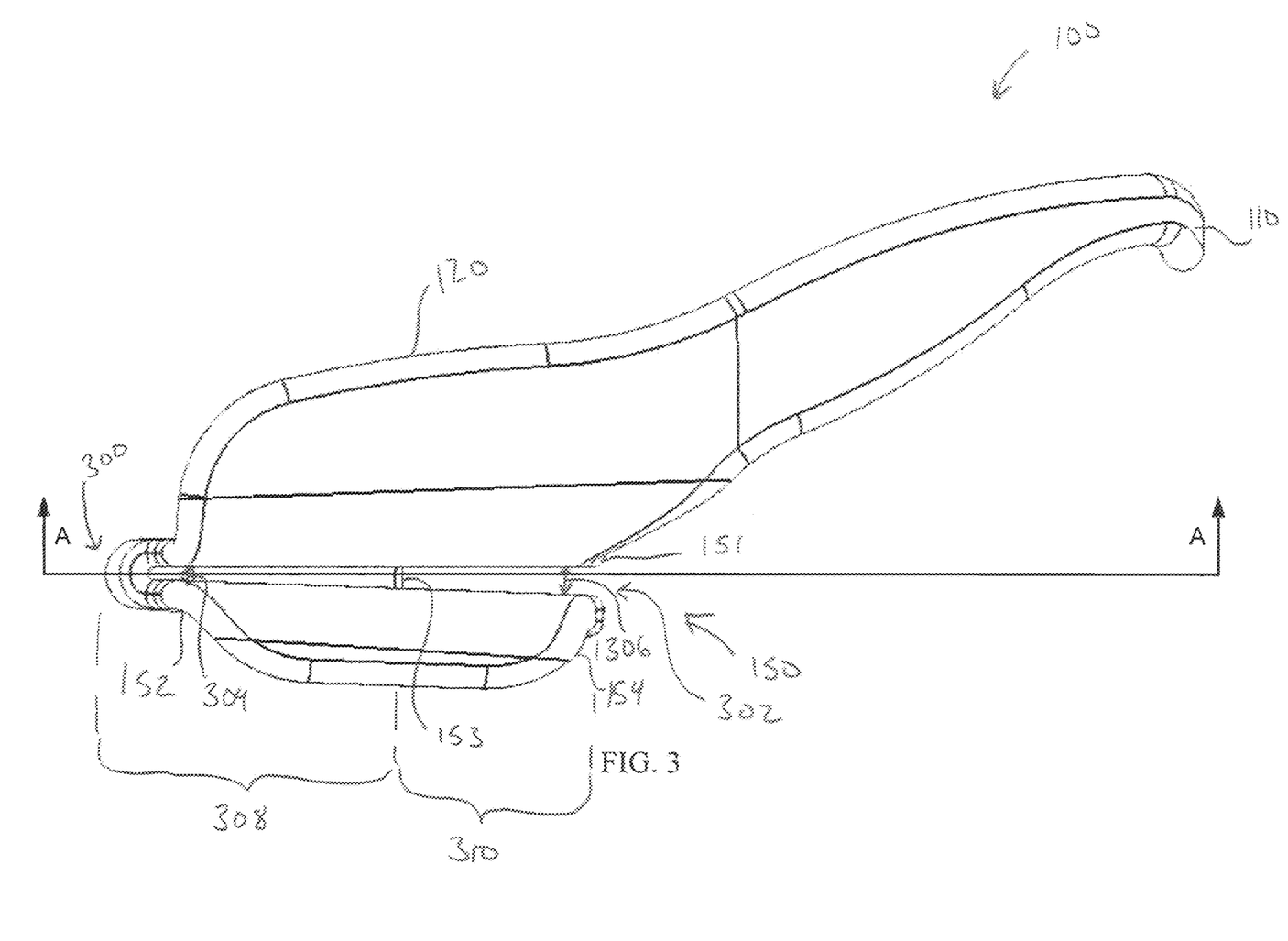
FIG. 3 is a left side view of the bruxism treatment apparatus.
Figure 4:
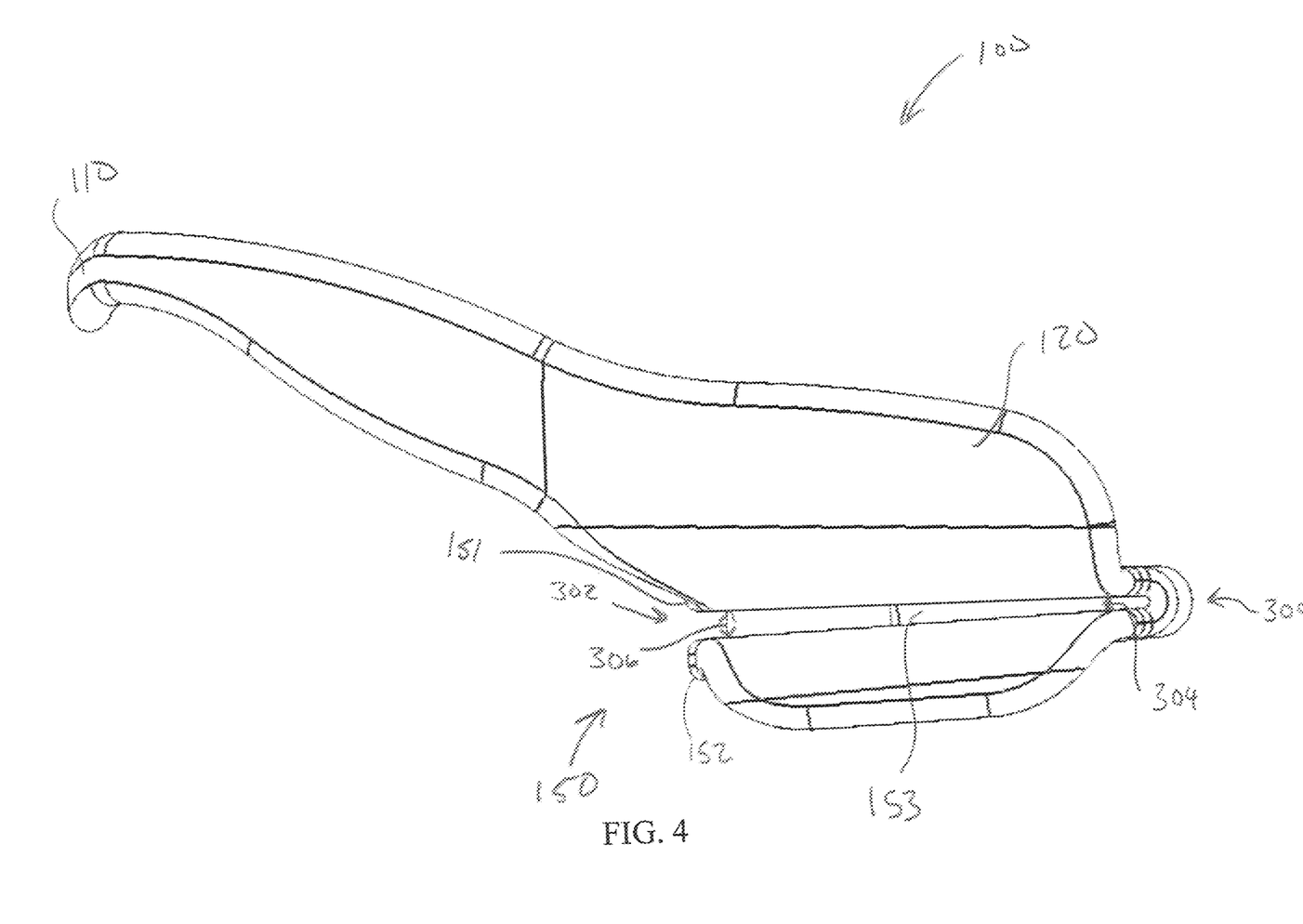
FIG. 4 is a right side view of the bruxism treatment apparatus.

As seen in FIG. 3, a left side view of the bruxism treatment apparatus, and in FIG. 4, a right side view of the bruxism treatment apparatus, the connecting member 153 can, in some embodiments, start at a back 300 and extends towards a front 302 of the projections 150. In some embodiments, the connecting member 153 can start at one of the sides of the projections 150 and extend towards the other of the sides of the projections, and in some embodiments, the connecting member 153 can start at the front 302 and extend towards the back 300 of the projections. The connecting member 153 can, as depicted in FIGS. 3 and 4, separate the top portion 151 from the bottom portion 152 by a distance, and specifically by a first distance 304 proximal to the back 300 of the protrusions 150 and a second distance 306 proximal to the front 302 of the protrusions 150. In some embodiments, the first and second distances 304, 306 can be the same, and in some embodiments, the first and second distances 304, 306 can be different. In the embodiment shown in FIG. 3, the first distance 304 is smaller than the second distance 306, and thus, the distance between the top portion 151 and the bottom portion 152 increases from the back 300 to the front 302 of the projections 150. In some embodiments, this increase in the distance between the top portion 151 and the bottom portion 152 from the back 300 to the front 302 of the projections 150 can provide significant benefits including, for example, better matching the anatomy of a mouth and particularly of a human mouth. For example, when the human jaw is a bit slack, the distance between the teeth in the back of the mouth is less than the distance between the teeth in the front of the mouth. Thus, the increasing separation between the top portion 151 and the bottom portion 152 shown in FIG. 3 can better fit a mouth, and additionally, as the mouth closes, this angle between the top and bottom portions 151, 152 can result in better and more equal distribution of force along the projections 150 and thus on the teeth.

As further seen, in some embodiments, the connecting member 153 extends partially from the back 300 to the front 302 of the projections 150. This partial extension creates a first portion 308, wherein the top portion 151 and the bottom portion 152 are rigidly connected and are non-displaceable with respect to each other a second portion, wherein the top portion 151 and the bottom portion 152 are displaceable with respect to each other. In the first portion 308, the distance between the top portion 151 and the bottom portion 152 is constant, whereas in the second portion 310, the distance between the top portion 151 and the bottom portion 152 are non-constant as the biting on the projections 150 results in the plastic and/or elastic deformation of all or portions of the second portion 310 to thereby decrease the distance between top 151 and bottom 152 in the second portion 310. Because of the rigid connection of the top portion 151 and the bottom portion 152 in the first portion 308, the top portion 151 and the bottom portion 152 are never parallel and never form a planar member and the deformation of the parts of the projections 150 in the second portion 310 leads to both the top portion 151 and the bottom portion 152 being non-planar.

Figure 5:
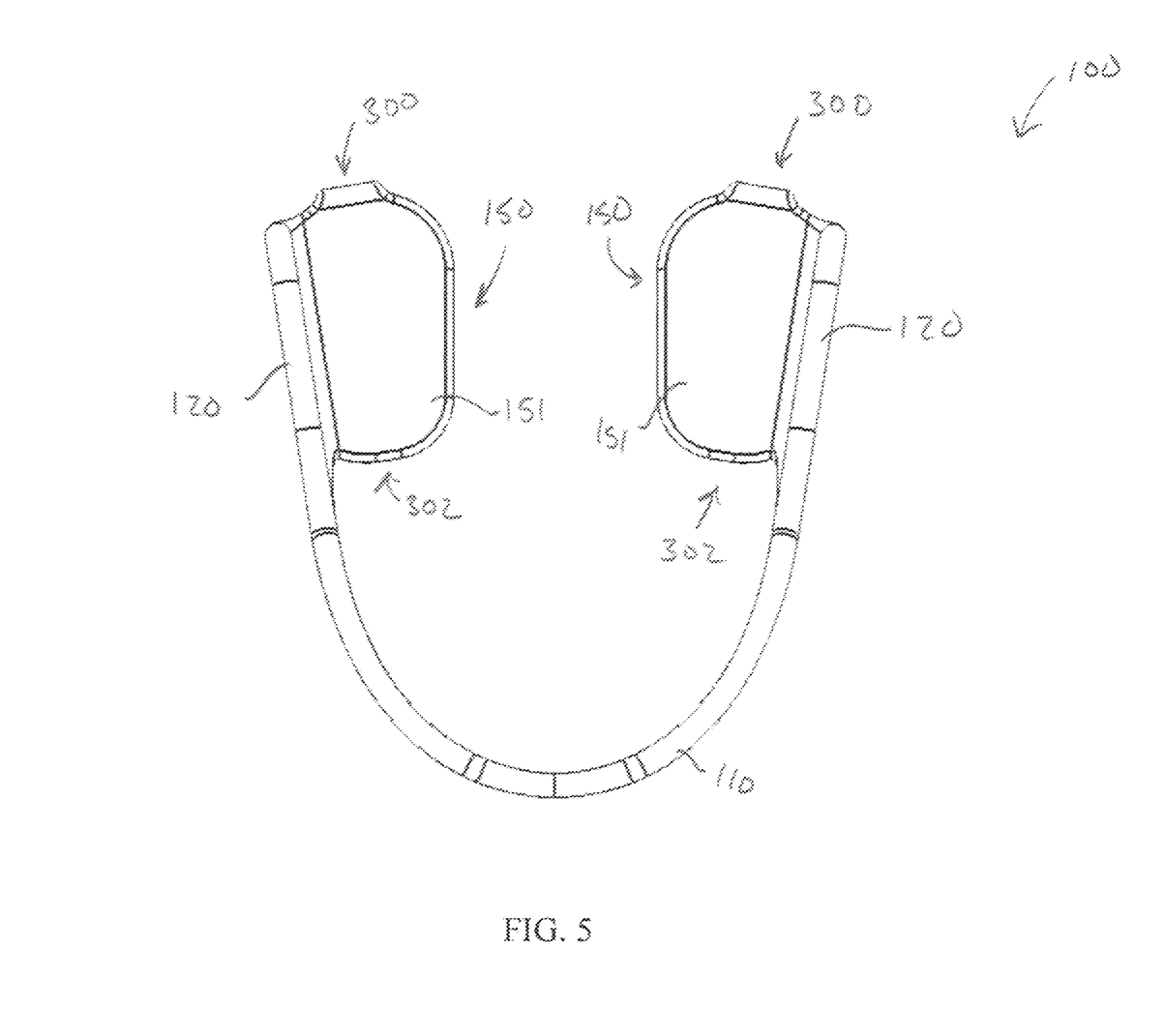
FIG. 5 is a top view of the bruxism treatment apparatus.
Figure 6:
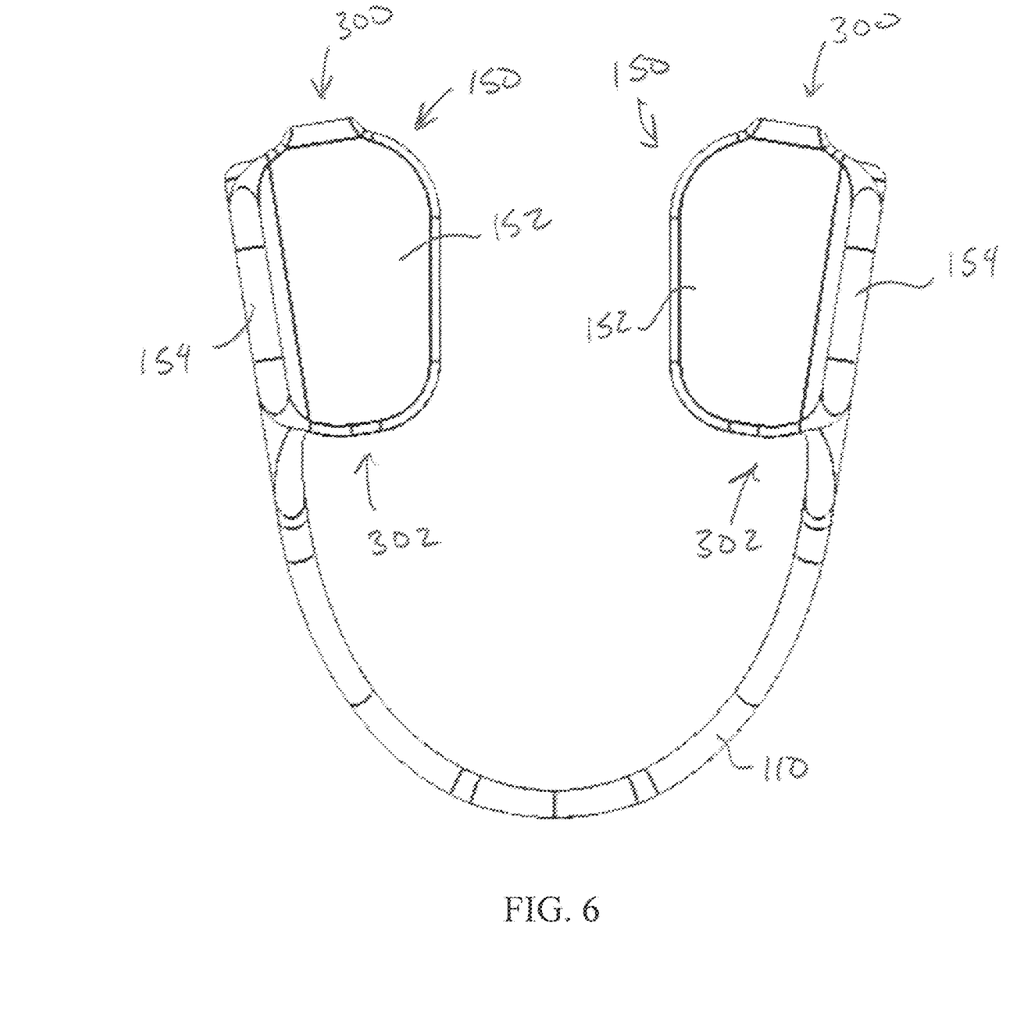
FIG. 6 is a bottom view of the bruxism treatment apparatus.
Figure 7:
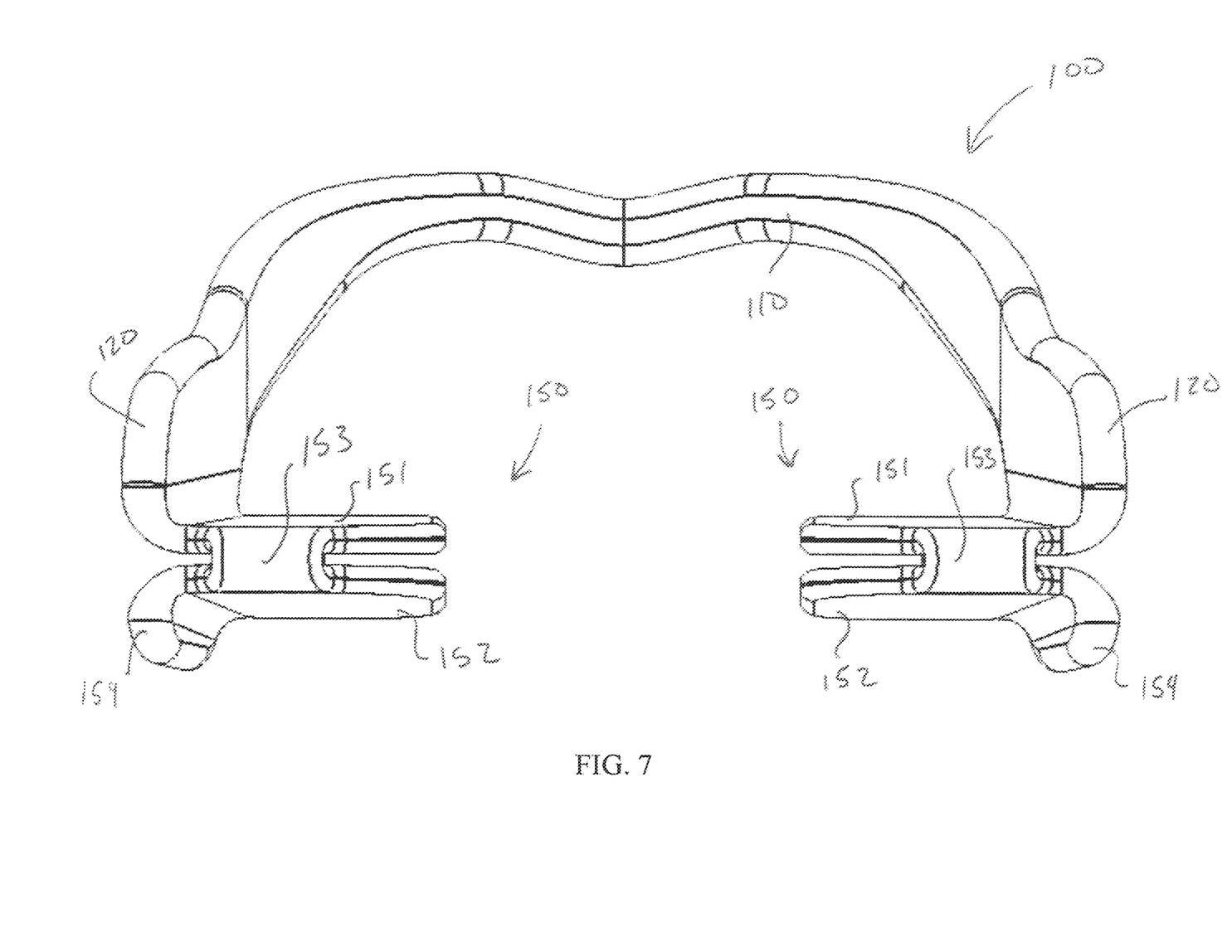
FIG. 7 is a back side view of the bruxism treatment apparatus.

As further in FIG. 5, a top view of the dental apparatus 100, top portion 151 of the projections 150 extend from the back portions 120 inwardly towards the opposing back portion 120 and the opposing projection 150. In contrast to this, and as shown in FIG. 6, a bottom view of the dental apparatus 100, the bottom portions 152 extend inwardly from the lip 154 and are not connected to the back portions 120. This separation between the bottom portions 152 and the back portions 120 is seen in FIG. 7, a back view of the dental apparatus 100. As seen in this figure, the bottom portion 152 is only connected to the top portion 151 via the connecting member 153.

Figure 8:
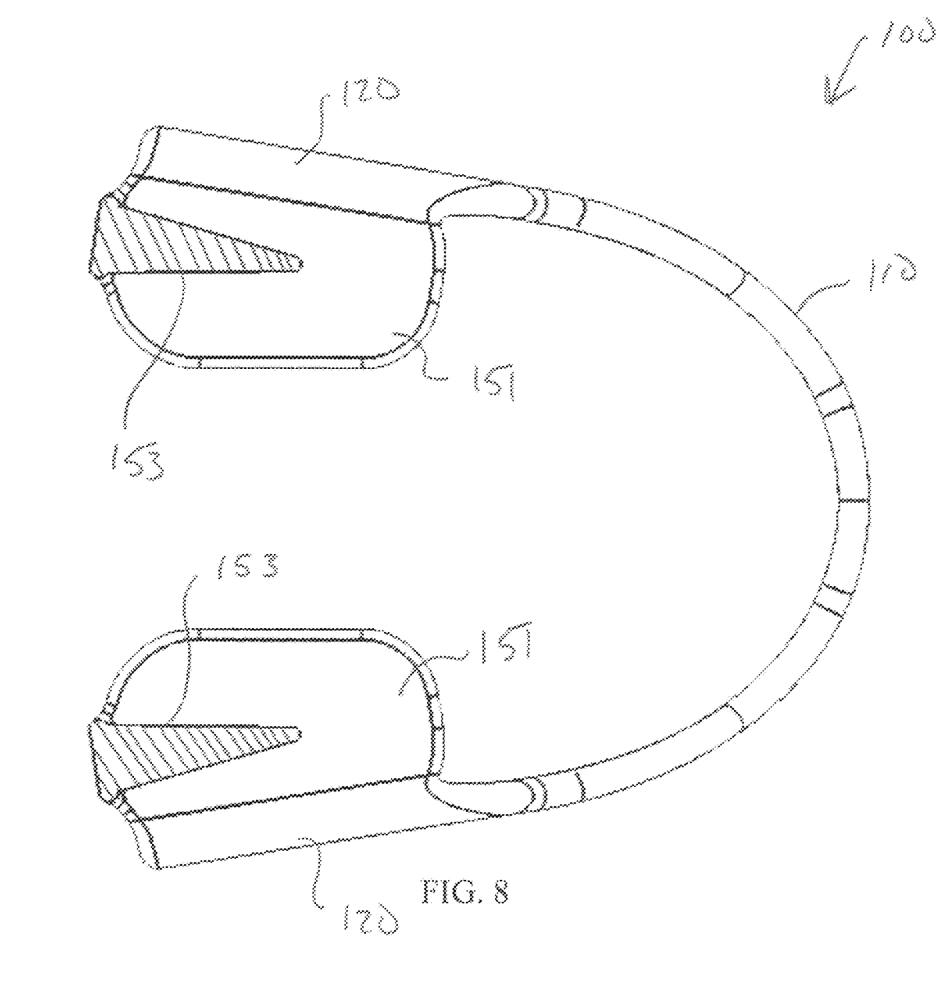
FIG. 8 is a section view taken along plane A shown in FIG. 2.

The connecting member 153 can comprise a variety of shapes and sizes. In the embodiment shown in FIGS. 3 and 4 and in FIG. 8, a section view taken along plane A shown in FIG. 2, the connecting member 153 can comprise a wedge-shaped member having a triangular cross-section. In some embodiments, the shape of the cross-section of the connecting member 153 can facilitate in providing desired levels of cushioning and/or support to teeth within the mouth. Further, in some embodiments, the wedge-shape and/or the triangular cross section can help to resist the relative twisting, displacement, and/or moving of one or both of the top portions 151 with respect to one or both of the bottom portions 152 during use, and specifically during heavy clenching or grinding (bruxing).

While various embodiments of present invention have been described, it will be apparent to those of skill in the art that many more embodiments and implementations are possible that are within the scope of this invention. Accordingly, the present invention is not to be limited to the described embodiments.

What is claimed is:

1. A dental apparatus comprising:
A curved portion;
first and second back portions connected to the curved portion, the curved portion and the first and second back portions together defining a U-shape; and
a first projection extending inwardly from the first back portion and a second projection extending inwardly from the second back portion, wherein the first projection and the second projection exclusively extend inwardly from the U-shape, wherein each of the first and second projections comprises a top portion separated from a bottom portion by a connecting member, wherein the top portion of the first projection connects to the first back portion and the top portion of the second projection connects to the second back portion, wherein the bottom portion of the first projection is not directly connected to the first back portion and the bottom portion of the second projection is not directly connected to the second back portion, and wherein the connecting member comprises a wedge having a thickness increasing from a back towards a front of each of the first and second projections and a triangular cross-section, wherein the triangular cross section of the connecting member is in a plane positioned between but not intersecting with the top and bottom portions of each of the first and second projections, and wherein the connecting member further comprises a curved protrusion extending from the back of the first and second projections.

2. The dental apparatus of claim 1, wherein the top portion and the bottom portion of each of the first and second projections are non-parallel relative to each other.

3. The dental apparatus of claim 1, wherein each connecting member extends from a back towards a front of each of the first and second projections.

4. The dental apparatus of claim 3, wherein each connecting member partially extends from a back towards a front of each of the first and second projections.

5. The dental apparatus of claim 4, wherein each connecting member partially extends from the back towards the front of the first and second projections to create a first portion and a second portion of each of the first and second projections.

6. The dental apparatus of claim 5, wherein the top portion is rigidly connected to the bottom portion of each of the first and second projections in the first portion.

7. The dental apparatus of claim 6, wherein the top portion and the bottom portion of each of the first and second projections are non-rigidly connected in the second portion.

8. The dental apparatus of claim 3, wherein each connecting member fully extends from a back towards a front of each of the first and second projections.

9. The dental apparatus of claim 1, wherein a space between the top portion and the bottom portion of each of the first and second projections is non-constant between the back and the front of each of the first and second projections.

10. The dental apparatus of claim 9, wherein the space between the top portion and the bottom portion of each of the first and second projections progressively increases from the back to the front of each of the first and second projections.

11. The dental apparatus of claim 9, wherein a distance between the top portion and the bottom portion of each of the first and second projections is greater at the front of each of the first and second projections than at the back of each of the first and second projections.

12. The dental apparatus of claim 9, further comprising a lip partially extending around the bottom portion of each of the first and second projections.

13. The dental apparatus of claim 9, wherein the bottom portion of the first projection is only coupled to the first back portion via the wedge-shaped connecting member.

14. A bruxism device comprising:
a first back portion;
a second back portion;
a curved portion connected to the first and second back portions, the curved portion and the first and second back portions defining a U-shape; and a pair of projections comprising: a first projection extending inwardly from the first back portion; and a second projection extending inwardly from the second back portion,
wherein each of the first and second projections comprises a top member separated from a bottom member by a wedge-shaped connecting member connecting the top member to the bottom member, the wedge-shaped connecting member having a thickness increasing from a back towards a front of each of the first and second projections and a triangular cross-section, wherein the triangular cross-section of the wedge-shaped connecting member is in a plane positioned between but not intersecting with the top and bottom portions of each of the first and second projections, wherein the bottom member of the first projection is not directly connected to the first back portion, and wherein the connecting member further comprises a curved protrusion extending from the back of the first and second projections.

15. The bruxism device of claim 14, wherein the bottom member of first projection is only coupled to the first back portion via the wedge-shaped connecting member.

16. The bruxism device of claim 14, wherein the top member and the bottom member of each of the first and second projections are non-parallel relative to each other.

17. The bruxism device of claim 14, wherein the wedge-shaped connecting member extends from a back towards a front of each of the first and second projections.

18. The bruxism device of claim 14, wherein the wedge-shaped connecting member partially extends from a back towards a front of each of the first and second projections, and wherein the wedge-shaped connecting member partially extends from the back towards the front of each of the first and second projection to create a first portion and a second portion of each of the first and second projections.

19. The bruxism device of claim 18, wherein the top member is rigidly connected to the bottom member of each of the first and second projections in the first portion.

\* \* \* \* \*